(12) United States Patent
Beasley et al.

(10) Patent No.: US 8,228,347 B2
(45) Date of Patent: Jul. 24, 2012

(54) USER INTERFACE AND METHODS FOR SONOGRAPHIC DISPLAY DEVICE

(75) Inventors: Jimmy C. Beasley, Phoenix, AZ (US); Eddie K. Burnside, Grantsville, UT (US); Rodney Scruggs, Salt Lake City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 501 days.

(21) Appl. No.: 11/745,756

(22) Filed: May 8, 2007

(65) Prior Publication Data

US 2008/0033293 A1 Feb. 7, 2008

Related U.S. Application Data

(60) Provisional application No. 60/746,741, filed on May 8, 2006.

(51) Int. Cl.
G09G 5/00 (2006.01)
A61B 8/00 (2006.01)
(52) U.S. Cl. .......................................... 345/665; 600/437
(58) Field of Classification Search ............ 600/437–468, 600/433–435
See application file for complete search history.

(56) References Cited

U.S. PATENT DOCUMENTS

| | | | |
|---|---|---|---|
| 3,858,325 A | 1/1975 | Goerler | 33/199 |
| 4,141,347 A | 2/1979 | Green et al. | 128/2 |
| 4,280,047 A | 7/1981 | Enos | 250/252 |
| 4,520,671 A | 6/1985 | Hardin | |
| 5,182,728 A * | 1/1993 | Shen et al. | 367/7 |
| 5,285,785 A | 2/1994 | Meyer | 128/653 |
| 5,305,203 A * | 4/1994 | Raab | 606/1 |
| 5,325,293 A | 6/1994 | Dorne | |
| 5,400,513 A * | 3/1995 | Duffield | 33/1 B |
| 5,416,816 A | 5/1995 | Wenstrup et al. | 378/18 |
| 5,534,952 A | 7/1996 | Zanecchia et al. | 351/200 |
| 5,609,485 A | 3/1997 | Bergman et al. | |
| 5,722,412 A | 3/1998 | Pflugrath et al. | |
| 5,795,297 A * | 8/1998 | Daigle | 600/447 |
| 5,817,024 A | 10/1998 | Ogle et al. | |
| 5,893,363 A | 4/1999 | Little et al. | |
| 5,908,387 A | 6/1999 | LeFree et al. | 600/425 |

(Continued)

FOREIGN PATENT DOCUMENTS

WO    WO-9838486 A    9/1998

(Continued)

OTHER PUBLICATIONS

Aug. 11, 2008, Written Opinion of the International Search Authority in international application PCT/US2007/011192.

(Continued)

*Primary Examiner* — Joni Hsu
*Assistant Examiner* — David H Chu
(74) *Attorney, Agent, or Firm* — Rutan & Tucker, LLP

(57) ABSTRACT

A user interface for a sonographic device is disclosed that displays a sonographic image and at least one reference object corresponding to a catheter size. The reference object may be scaled in proportion to the sonographic image. In addition, the user interface may further display a plurality of vertical lines and a plurality of horizontal lines arranged in a grid-like pattern and placed over the sonographic image. The size of both the sonographic image and the at least one reference object may change in proportion to a chosen insertion depth. A display device, a sonographic device and corresponding methods are also disclosed.

29 Claims, 6 Drawing Sheets

U.S. PATENT DOCUMENTS

| | | |
|---|---|---|
| 5,920,317 A | 7/1999 | McDonald |
| 5,970,119 A | 10/1999 | Hofmann |
| 6,019,724 A | 2/2000 | Gronningsaeter et al. |
| 6,048,314 A | 4/2000 | Nikom |
| 6,063,030 A | 5/2000 | Vara et al. |
| 6,063,032 A | 5/2000 | Grunwald |
| 6,117,079 A | 9/2000 | Brackett et al. |
| 6,132,373 A | 10/2000 | Ito et al. |
| 6,132,379 A | 10/2000 | Patacsil et al. |
| 6,135,961 A | 10/2000 | Pflugrath et al. |
| 6,154,576 A | 11/2000 | Anderson et al. ............ 382/269 |
| 6,203,498 B1 | 3/2001 | Bunce et al. |
| 6,213,944 B1 | 4/2001 | Miller et al. |
| 6,231,231 B1 | 5/2001 | Farrokhnia et al. ........... 378/207 |
| 6,251,072 B1 | 6/2001 | Ladak et al. |
| 6,360,116 B1 * | 3/2002 | Jackson et al. ................ 600/427 |
| D456,509 S | 4/2002 | Schultz |
| 6,364,839 B1 | 4/2002 | Little et al. |
| 6,371,918 B1 | 4/2002 | Bunce |
| 6,379,302 B1 | 4/2002 | Kessman et al. |
| 6,383,139 B1 | 5/2002 | Hwang et al. |
| 6,413,217 B1 | 7/2002 | Mo |
| 6,416,475 B1 | 7/2002 | Hwang et al. |
| D461,895 S | 8/2002 | Barnes et al. |
| 6,443,894 B1 | 9/2002 | Sumanaweera et al. |
| 6,447,451 B1 | 9/2002 | Wing et al. |
| 6,450,978 B1 * | 9/2002 | Brosseau et al. ............. 600/595 |
| 6,468,212 B1 | 10/2002 | Scott et al. |
| 6,471,651 B1 | 10/2002 | Hwang et al. |
| 6,485,422 B1 * | 11/2002 | Mikus et al. .................. 600/439 |
| 6,511,427 B1 | 1/2003 | Sliwa, Jr. et al. |
| 6,512,942 B1 * | 1/2003 | Burdette et al. .............. 600/427 |
| 6,516,215 B1 | 2/2003 | Roundhill |
| 6,524,247 B2 | 2/2003 | Zhao et al. |
| 6,569,101 B2 | 5/2003 | Quistgaard et al. |
| 6,575,908 B2 | 6/2003 | Barnes et al. |
| 6,579,262 B1 | 6/2003 | Mick et al. .................... 604/116 |
| 6,592,565 B2 | 7/2003 | Twardowski |
| 6,604,630 B1 | 8/2003 | Cabatic et al. |
| 6,638,223 B2 | 10/2003 | Lifshitz et al. |
| 6,648,826 B2 | 11/2003 | Little et al. |
| 6,687,386 B1 | 2/2004 | Ito et al. |
| 6,702,763 B2 | 3/2004 | Murphy et al. ............... 600/587 |
| 6,754,608 B2 | 6/2004 | Svanerudh et al. |
| D496,596 S | 9/2004 | Dalrymple ...................... D10/64 |
| 6,793,391 B2 | 9/2004 | Zimmermann ............... 378/205 |
| 6,817,982 B2 | 11/2004 | Fritz et al. |
| 6,835,177 B2 | 12/2004 | Fritz et al. |
| 6,857,196 B2 | 2/2005 | Dalrymple ........................ 33/512 |
| 6,863,655 B2 | 3/2005 | Bjaerum et al. .............. 600/442 |
| 6,928,146 B2 | 8/2005 | Broyles et al. ................ 378/164 |
| D509,900 S | 9/2005 | Barnes et al. |
| 6,941,166 B2 | 9/2005 | MacAdam et al. .......... 600/521 |
| 6,962,566 B2 | 11/2005 | Quistgaard et al. |
| 6,968,227 B2 | 11/2005 | MacAdam et al. .......... 600/515 |
| 6,979,294 B1 | 12/2005 | Selzer et al. |
| 7,006,955 B2 | 2/2006 | Daft et al. |
| 7,022,075 B2 | 4/2006 | Grunwald et al. |
| 7,169,108 B2 | 1/2007 | Little et al. |
| 7,174,201 B2 | 2/2007 | Govari et al. ................. 600/424 |
| D538,432 S | 3/2007 | Diener et al. |
| 7,223,242 B2 | 5/2007 | He et al. |
| D544,962 S | 6/2007 | Diener et al. |
| D558,351 S | 12/2007 | Diener et al. |
| D559,390 S | 1/2008 | Diener et al. |
| 7,349,522 B2 * | 3/2008 | Yan et al. .......................... 378/65 |
| 7,449,640 B2 | 11/2008 | Coleman |
| 7,453,472 B2 | 11/2008 | Goede et al. |
| 7,457,672 B2 | 11/2008 | Katsman et al. |
| 7,466,323 B2 | 12/2008 | Krishnamurthy et al. |
| D591,423 S | 4/2009 | Diener et al. |
| D592,750 S | 5/2009 | Diener et al. |
| D592,760 S | 5/2009 | Diener et al. |
| 7,534,211 B2 | 5/2009 | Hwang et al. |
| 7,549,961 B1 | 6/2009 | Hwang |
| 7,588,541 B2 | 9/2009 | Floyd et al. |
| 7,591,786 B2 | 9/2009 | Holmberg et al. |
| 7,599,730 B2 * | 10/2009 | Hunter et al. ................. 600/424 |
| 7,604,596 B2 | 10/2009 | Hwang et al. |
| 7,604,601 B2 | 10/2009 | Altmann et al. |
| 7,606,402 B2 | 10/2009 | Heimdal et al. |
| 7,643,040 B1 | 1/2010 | Gabrielson et al. |
| 7,656,418 B2 | 2/2010 | Watkins et al. |
| 7,686,766 B2 | 3/2010 | Quistgaard et al. |
| 7,694,814 B1 | 4/2010 | Cristobal et al. |
| 7,724,680 B2 | 5/2010 | Karlsson |
| 7,727,153 B2 | 6/2010 | Fritz et al. |
| 7,728,821 B2 | 6/2010 | Hillis et al. |
| 7,740,586 B2 | 6/2010 | Hwang et al. |
| D625,014 S | 10/2010 | Hansen et al. |
| D625,015 S | 10/2010 | Hansen et al. |
| 7,809,400 B1 | 10/2010 | Hwang |
| 7,819,807 B2 | 10/2010 | Barnes et al. |
| 7,831,449 B2 | 11/2010 | Ying et al. |
| 7,840,040 B2 | 11/2010 | Wilcox et al. |
| 7,846,098 B2 | 12/2010 | Bakircioglu et al. |
| 7,849,250 B2 | 12/2010 | Diener et al. |
| 7,867,168 B2 | 1/2011 | Little et al. |
| 7,876,945 B2 | 1/2011 | Lotjonen |
| 7,883,467 B2 | 2/2011 | Akaki et al. |
| 7,955,265 B2 | 6/2011 | Burla et al. |
| 7,978,461 B2 | 7/2011 | Diener et al. |
| 7,996,688 B2 | 8/2011 | Little |
| 8,004,572 B2 | 8/2011 | Figueredo et al. |
| 8,007,438 B2 | 8/2011 | Osaka et al. |
| 8,025,622 B2 | 9/2011 | Rold et al. |
| 2001/0056235 A1 | 12/2001 | Quistgaard et al. |
| 2002/0056047 A1 | 5/2002 | Lehman |
| 2002/0143256 A1 | 10/2002 | Wing et al. |
| 2002/0173721 A1 | 11/2002 | Grunwald et al. |
| 2002/0177774 A1 | 11/2002 | Hwang et al. |
| 2002/0193686 A1 | 12/2002 | Gilboa |
| 2003/0009102 A1 | 1/2003 | Quistgaard et al. |
| 2003/0013965 A1 | 1/2003 | Quistgaard et al. |
| 2003/0013966 A1 | 1/2003 | Barnes et al. |
| 2003/0047126 A1 | 3/2003 | Tomaschko |
| 2003/0069897 A1 * | 4/2003 | Roy et al. .................... 707/104.1 |
| 2003/0074650 A1 | 4/2003 | Akgul et al. |
| 2003/0078501 A1 | 4/2003 | Barnes et al. |
| 2003/0141205 A1 | 7/2003 | Cabatic et al. |
| 2003/0163047 A1 | 8/2003 | Little et al. |
| 2003/0195418 A1 | 10/2003 | Barnes et al. |
| 2003/0199762 A1 | 10/2003 | Fritz et al. |
| 2004/0015079 A1 | 1/2004 | Berger et al. |
| 2004/0066398 A1 | 4/2004 | Dolimier et al. |
| 2004/0099815 A1 * | 5/2004 | Sfez et al. .................... 250/492.1 |
| 2004/0111183 A1 * | 6/2004 | Sutherland et al. ........... 700/245 |
| 2004/0116808 A1 | 6/2004 | Fritz et al. |
| 2004/0133110 A1 | 7/2004 | Little et al. |
| 2004/0138564 A1 | 7/2004 | Hwang et al. |
| 2004/0143181 A1 * | 7/2004 | Damasco et al. ............. 600/411 |
| 2004/0150963 A1 | 8/2004 | Holmberg et al. |
| 2004/0152982 A1 | 8/2004 | Hwang et al. |
| 2004/0169673 A1 * | 9/2004 | Crampe et al. ................. 345/700 |
| 2004/0215072 A1 * | 10/2004 | Zhu ................................ 600/407 |
| 2004/0240715 A1 * | 12/2004 | Wicker et al. .................. 382/128 |
| 2005/0020911 A1 * | 1/2005 | Viswanathan et al. ........ 600/424 |
| 2005/0054917 A1 * | 3/2005 | Kitson ........................... 600/427 |
| 2005/0075544 A1 * | 4/2005 | Shapiro et al. ................ 600/300 |
| 2005/0096528 A1 | 5/2005 | Fritz et al. |
| 2005/0101868 A1 * | 5/2005 | Ridley et al. .................. 600/459 |
| 2005/0107688 A1 * | 5/2005 | Strommer ...................... 600/424 |
| 2005/0119555 A1 | 6/2005 | Fritz et al. |
| 2005/0124885 A1 * | 6/2005 | Abend et al. .................. 600/443 |
| 2005/0131291 A1 | 6/2005 | Floyd et al. |
| 2005/0215896 A1 * | 9/2005 | McMorrow et al. .......... 600/437 |
| 2005/0215904 A1 * | 9/2005 | Sumanaweera et al. ...... 600/458 |
| 2005/0228276 A1 * | 10/2005 | He et al. ........................ 600/437 |
| 2005/0228287 A1 | 10/2005 | Little et al. |
| 2005/0235272 A1 | 10/2005 | Skinner |
| 2005/0265267 A1 | 12/2005 | Hwang |
| 2005/0288586 A1 * | 12/2005 | Ferek-Petric ................. 600/443 |
| 2006/0015039 A1 | 1/2006 | Cassidy et al. |
| 2006/0020206 A1 | 1/2006 | Serra et al. |
| 2006/0025684 A1 | 2/2006 | Quistgaard et al. |
| 2006/0058652 A1 | 3/2006 | Little |
| 2006/0058655 A1 | 3/2006 | Little |

| | | |
|---|---|---|
| 2006/0058663 A1* | 3/2006 | Willis et al. .................. 600/437 |
| 2006/0085068 A1* | 4/2006 | Barry ......................... 623/17.11 |
| 2006/0111634 A1* | 5/2006 | Wu .............................. 600/443 |
| 2006/0116578 A1 | 6/2006 | Grunwald et al. |
| 2006/0173303 A1* | 8/2006 | Yu et al. ....................... 600/437 |
| 2006/0174065 A1 | 8/2006 | Kuzara et al. |
| 2006/0253032 A1 | 11/2006 | Altmann et al. |
| 2007/0049822 A1 | 3/2007 | Bunce et al. |
| 2007/0071266 A1 | 3/2007 | Little et al. |
| 2007/0085452 A1 | 4/2007 | Coleman |
| 2007/0116373 A1 | 5/2007 | Hwang et al. |
| 2007/0121769 A1 | 5/2007 | Gabrielson et al. |
| 2007/0127792 A1* | 6/2007 | Virtue ........................... 382/128 |
| 2007/0199848 A1 | 8/2007 | Ellswood et al. |
| 2007/0232910 A1 | 10/2007 | Hwang et al. |
| 2007/0239008 A1 | 10/2007 | Nakajima et al. |
| 2007/0239019 A1 | 10/2007 | Richard et al. |
| 2007/0239021 A1 | 10/2007 | Oonuki et al. |
| 2007/0258632 A1* | 11/2007 | Friedman et al. ............. 382/128 |
| 2007/0271507 A1* | 11/2007 | Connor et al. ................ 715/530 |
| 2007/0282263 A1* | 12/2007 | Kalafut et al. ................ 604/131 |
| 2008/0033759 A1 | 2/2008 | Finlay |
| 2008/0099638 A1 | 5/2008 | Diener et al. |
| 2008/0104300 A1 | 5/2008 | Diener et al. |
| 2008/0119731 A1 | 5/2008 | Becerra et al. |
| 2008/0137922 A1 | 6/2008 | Catallo et al. |
| 2008/0141107 A1 | 6/2008 | Catallo et al. |
| 2008/0144896 A1 | 6/2008 | Burke |
| 2008/0183079 A1 | 7/2008 | Lundberg |
| 2008/0208047 A1 | 8/2008 | Delso |
| 2008/0247618 A1 | 10/2008 | Laine et al. |
| 2008/0249407 A1 | 10/2008 | Hill et al. |
| 2008/0287789 A1 | 11/2008 | Hwang et al. |
| 2008/0310816 A1 | 12/2008 | Allen et al. |
| 2009/0043195 A1* | 2/2009 | Poland .......................... 600/437 |
| 2009/0069681 A1 | 3/2009 | Lundberg et al. |
| 2009/0069725 A1 | 3/2009 | Diener et al. |
| 2009/0076385 A1 | 3/2009 | Jackson et al. |
| 2009/0143672 A1 | 6/2009 | Harms et al. |
| 2009/0171212 A1 | 7/2009 | Garon |
| 2009/0270722 A1 | 10/2009 | Floyd et al. |
| 2009/0275835 A1 | 11/2009 | Hwang et al. |
| 2010/0053197 A1 | 3/2010 | Gabrielson et al. |
| 2010/0081930 A1 | 4/2010 | Dunbar |
| 2010/0094132 A1 | 4/2010 | Hansen et al. |
| 2010/0121189 A1 | 5/2010 | Ma et al. |
| 2010/0121190 A1 | 5/2010 | Pagoulatos et al. |
| 2010/0121196 A1 | 5/2010 | Hwang et al. |
| 2010/0130855 A1 | 5/2010 | Lundberg et al. |
| 2010/0145195 A1 | 6/2010 | Hyun |
| 2010/0260398 A1 | 10/2010 | Ma et al. |
| 2010/0274131 A1 | 10/2010 | Barnes et al. |
| 2010/0295870 A1 | 11/2010 | Baghdadi et al. |
| 2011/0066031 A1 | 3/2011 | Lee et al. |
| 2011/0152684 A1 | 6/2011 | Altmann et al. |
| 2011/0234630 A1 | 9/2011 | Batman et al. |

FOREIGN PATENT DOCUMENTS

| | | |
|---|---|---|
| WO | WO-0124704 A | 4/2001 |
| WO | WO 2005/008418 | 1/2005 |

OTHER PUBLICATIONS

Sep. 25, 2009 International Search Report in international application PCT/US2007/011192.

Nov. 11, 2008 International Preliminary Report on Patentability in international application PCT/US2007/011192.

EP 07874457.0 filed May 8, 2007 Office Action dated May 31, 2011.

* cited by examiner

USER INTERFACE AND METHODS FOR SONOGRAPHIC DISPLAY DEVICE

RELATED APPLICATION

This application claims the benefit under 35 U.S.C. §119(e) of U.S. Provisional Application No. 60/746,741, entitled "SONOGRAPHIC DISPLAY DEVICE AND METHODS OF USE," filed May 8, 2006, which is hereby incorporated by reference herein in its entirety.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

Figure 1:
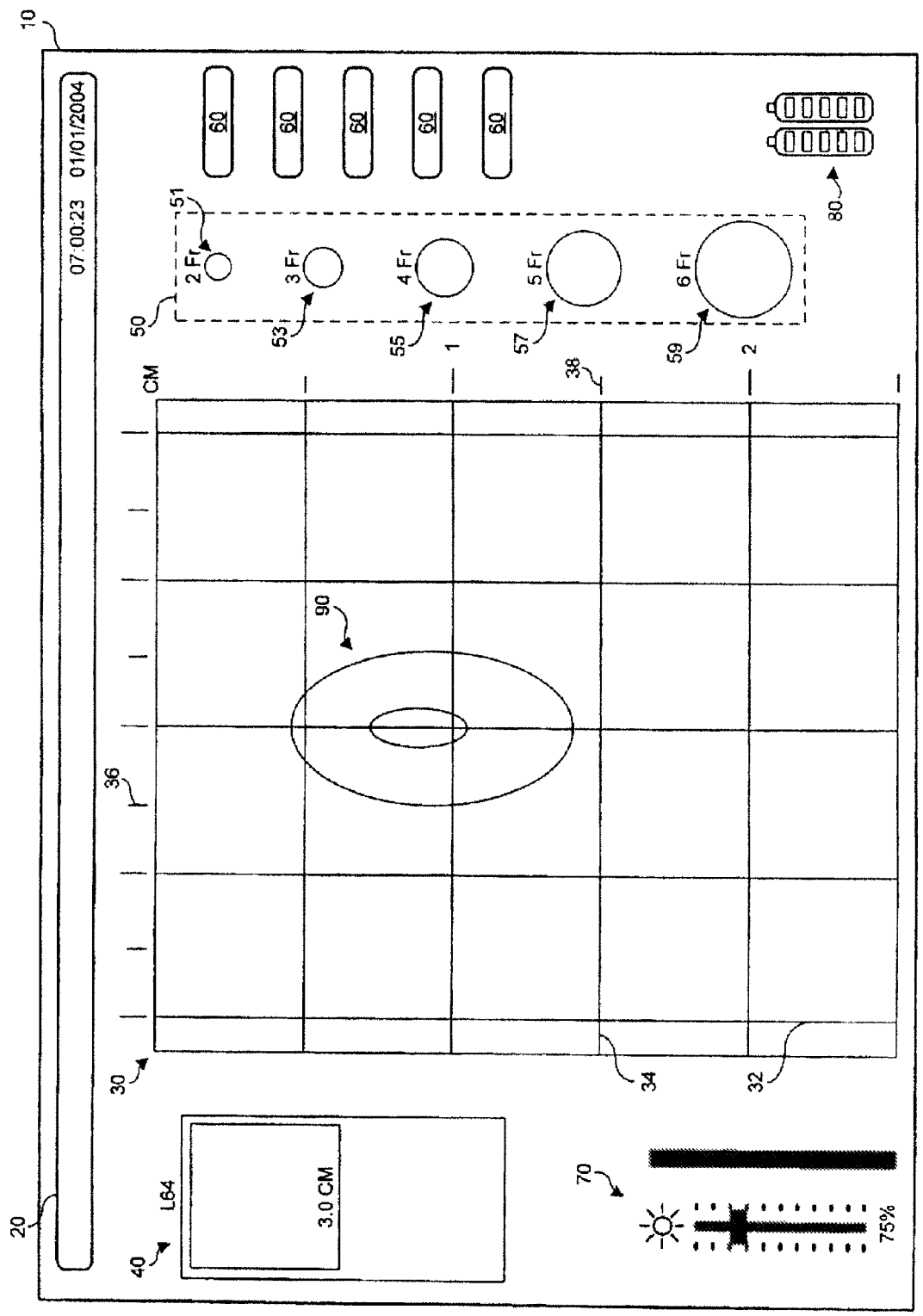
FIG. 1 is an illustration of a first view of an exemplary user interface for a sonographic device according to one embodiment.

A sonographic device is a diagnostic imaging device commonly used by medical professionals to visualize the size, structure, and/or condition of a patient's muscles, internal organs, vascular structures, or the like. Sonographic devices typically comprise a processing unit, a probe connected to the processing unit, and a display device in communication with the processing unit.

In certain embodiments described herein, a graphical user interface (generally referred to herein as a "user interface") for a sonographic system is used to select the size of a catheter for placement in a vascular structure. However, one of skill in the art will recognize from the disclosure herein that the systems and methods described herein are not so limited. For example, the systems and methods described herein may also be used to select needle sizes and/or the sizes of other devices for placement (e.g., intraoperatively or percutaneously) in vascular structures and/or various organs and structures of the body.

According to at least one embodiment, a user interface for a sonographic device may be configured to display a sonographic image and at least one reference object corresponding to a catheter size. In one embodiment, the reference object is circular and includes a diameter corresponding to a catheter size, such as an outer diameter of a catheter. In other embodiments, the reference object can be any other suitable shape.

In at least one embodiment, the at least one reference object is scaled in proportion to the sonographic image. In addition, the user interface may be configured to display a plurality of vertical lines and a plurality of horizontal lines arranged in a grid-like pattern and placed over the sonographic image. The area defined by a first vertical line and a second vertical line adjacent to the first vertical line may correspond to a dimensional measurement unit. Similarly, the area defined by a first horizontal line and a second horizontal line adjacent to the first horizontal line may correspond to a dimensional measurement unit. In certain embodiments, the size of both the sonographic image and the at least one reference object changes in proportion to a chosen insertion depth.

In at least one embodiment, the user interface is further configured to allow a user to select the catheter size corresponding to the first reference object. In addition, or in other embodiments, the user interface is further configured to selectively display a selected reference object over the sonographic image. For example, a user may drag or otherwise reposition a reference object from a first area of the user interface to a second area of the user interface over the sonographic image. The user may also be allowed to change the size of the selected reference object displayed over the sonographic image so as to correspond to a desired catheter size.

A method for displaying a sonographic image on a sonographic display device may comprise displaying a sonographic image on the sonographic display device, displaying a plurality of vertical and horizontal lines arranged in a grid-like pattern on the sonographic display device, and placing the grid-like pattern over the sonographic image. The method may also comprise displaying, on the sonographic display device, at least one reference object corresponding to a catheter size.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). In other embodiments, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

Several aspects of the embodiments described will be illustrated as software modules or components. As used herein, a software module or component may include any type of computer instruction or computer executable code located within a memory device. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Figure 2:
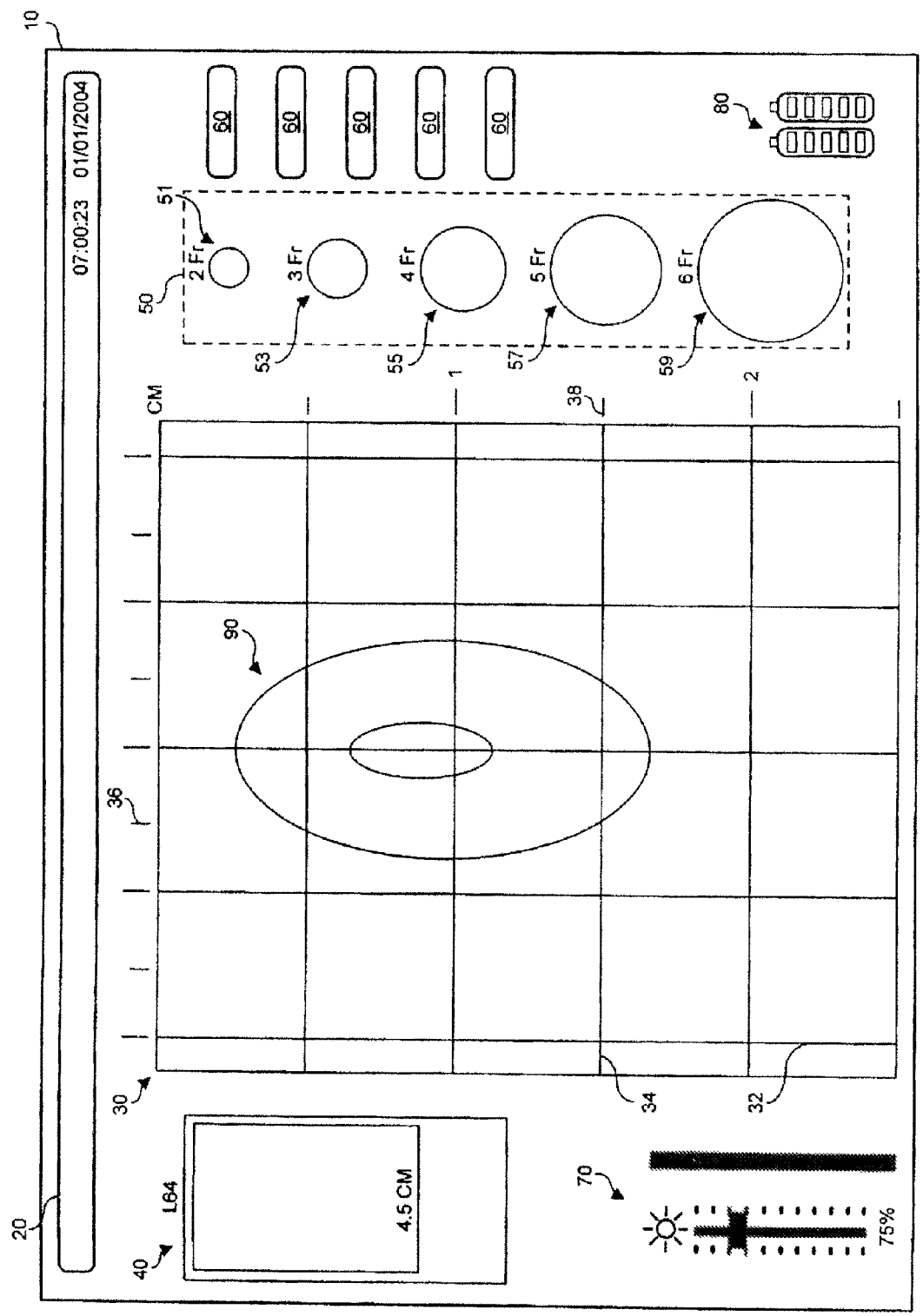
FIG. 2 is an illustration of a second view of an exemplary user interface for a sonographic device according to one embodiment.
Figure 3:
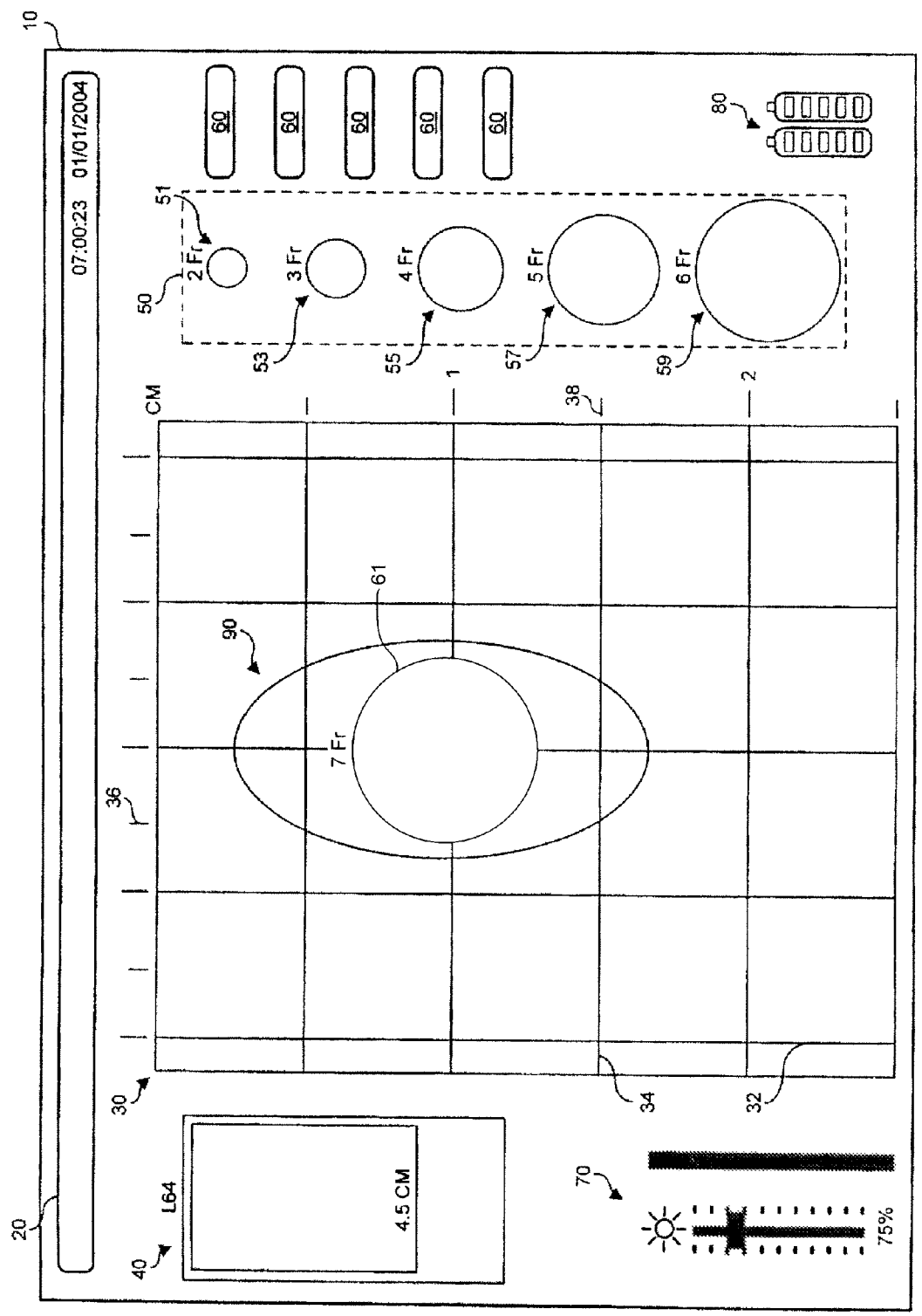
FIG. 3 is an illustration of a third view of an exemplary user interface for a sonographic device according to one embodiment.

Generally, one or more of the exemplary embodiments described and/or illustrated herein may be configured for use in connection with a sonographic device, also known as a sonograph, an ultrasonograph, or an ultrasound device. FIGS. 1-3 are illustrations of an exemplary user interface 10 for a sonographic device according to certain embodiments. The user interface 10 may be displayed on any display device capable of displaying sonographic images. The display device according to certain embodiments may be connected to a processing unit of a sonographic device. Optionally, as discussed below in relation to FIGS. 4 and 5, the display device may comprise a portion of, and be integrally formed with, a sonographic device.

In at least one embodiment, the user interface 10 may comprise a first display area 20 and a second display area 30. In certain embodiments, the first display area 20 may be configured to display text or graphics-based information. For example, the first display area 20 may be configured to display certain status information, such as the current date or time. The second display area 30 generally represents an area configured to display various sonographic images and/or data. In many embodiments, the second display area 30 may be configured to display a sonographic image 90. The sonographic image 90 generally represents any image generated using sonographic or ultrasonographic techniques, as known to those of ordinary skill in the art. In certain embodiments, the sonographic image 90 may depict the muscle, internal organs, or vasculature of a patient.

As seen in FIGS. 1-3, the user interface 10 may also include an insertion depth indicator 40. In at least one embodiment, the insertion depth indicator 40 displays an insertion depth for the sonographic image 90 displayed in the second display area 30. In other words, in this embodiment, the insertion depth indicator 40 indicates, graphically and/or using text, the distance (in measurement units, such as centimeters or inches) from the surface of a patient's skin to the cross-sectional image 90 displayed in the second display area 30. In certain embodiments, the insertion depth for the image 90 may range between about 1.5 cm to about 6 cm and may be chosen by an operator of the sonographic device.

In at least one embodiment, the size of the sonographic image 90 displayed in the second display area 30 may change as the insertion depth is varied by the operator of the sonographic device. That is, as the insertion depth is increased, the relative size of the sonographic image 90 displayed in the second display area 30 may also increase. In contrast, as the insertion depth is decreased, the relative size of the sonographic image 90 displayed in the second display area 30 may also decrease. For example, the size of the sonographic image 90 may increase as the insertion depth is increased from about 3.0 cm (illustrated in FIG. 1) to about 4.5 cm (illustrated in FIGS. 2 and 3).

As seen in FIGS. 1-3, the second display area 30 may also include a plurality of vertical reference lines 32 and a plurality of horizontal reference lines 34 arranged in a grid-like pattern over the sonographic image 90. In certain embodiments, the vertical reference lines 32 may be configured to extend from, and be in alignment with, a plurality of vertical reference marks 36 positioned along the periphery of the second display area 30. Similarly, the horizontal reference lines 34 may be configured to extend from, and be in alignment with, a plurality of horizontal reference marks 38 positioned along the periphery of the second display area 30. In certain embodiments, a user may select whether or not to display the reference lines 32, 34 and/or the reference marks 36, 38.

In at least one embodiment, the area defined by adjacent vertical reference marks 36 may correspond to a dimensional measurement unit, such as a centimeter, inch, or a fraction thereof. Similarly, the area defined by adjacent horizontal reference marks 38 may correspond to a dimensional measurement unit, such as a centimeter, inch, or a fraction thereof. For example, each vertical reference mark 36 may be spaced exactly one-half of a centimeter apart from each adjacent vertical reference mark 36. Similarly, each horizontal reference mark 38 may be spaced exactly one-half or one-quarter of a centimeter apart from each adjacent horizontal reference mark 38.

As seen in FIGS. 1-3, the user interface 10 may also include a third display area 50 configured to display one or more reference circles 51, 53, 55, 57, 59. In certain embodiments, each reference circle displayed in the third display area 50 may be sized and shaped so as to correspond to a French catheter size. In other words, each reference circle may include an outer diameter that equals the outer diameter of a chosen catheter size. For example, the outer diameter of the reference circle 51 may correspond to the outer diameter of a 2 French catheter, the outer diameter of the reference circle 53 may correspond to the outer diameter of a 3 French catheter, the outer diameter of the reference circle 55 may correspond to the outer diameter of a 4 French catheter, the outer diameter of the reference circle 57 may correspond to the outer diameter of a 5 French catheter, and the outer diameter of the reference circle 59 may correspond to the outer diameter of a 6 French catheter.

One skilled in the art will recognize from the disclosure herein that the third display area 50 of the user interface 10 may display fewer than five reference circles or more than five reference circles. For example, in one embodiment, the third display area 50 displays seven reference circles (respectively corresponding to the outer diameter of a 2 French catheter, a 3 French catheter, a 4 French catheter, a 5 French catheter, a 6 French catheter, a 7 French catheter, and an 8 French catheter). In addition, or in other embodiments, a user may select the number of reference circles and the size of each reference circle to display in the third display area 50.

Further, as discussed above, one skilled in the art will recognize from the disclosure herein that the reference circles 51, 53, 55, 57, 59 or other icons displayed in the third display area 50 may correspond to the size of other objects besides catheters. For example, objects displayed in the third display area 50 may correspond to various needle sizes or the sizes of other insertable or implantable objects for vascular structures, organs or other bodily structures.

In at least one embodiment, the catheter sizes represented by each reference circle displayed in the third display area 50 may be accurately proportioned in size with the sonographic image 90 displayed in the second display area 30. That is, each reference circle displayed in the third display area 50 may be drawn on a 1:1 scale with the sonographic image 90. Thus, in certain embodiments, the various reference circles displayed in the third display area 50 may be used by a medical professional in determining a preferred catheter size for insertion within a patient. For example, by comparing one or more of the reference circles displayed in the third display area 50 with the sonographic image 90 displayed in the second display area 30, a medical professional may be able to determine the catheter size that will be best suited for insertion within, for example, the vasculature of a patient.

In at least one embodiment, the size of each reference circle displayed in the third display area 50 may vary in relation to a chosen insertion depth (imaging depth), indicated in the insertion depth indicator 40. In particular, the size of each reference circle displayed in the third display area 50 may increase or decrease as the insertion depth is increased or decreased, such that the scale between the sonographic image 90 and each catheter size displayed in the third display area 50 remains 1:1. For example, the size of each reference circle 51, 53, 55, 57, 59 may increase as an insertion depth is increased from about 3.0 cm (illustrated in FIG. 1) to about 4.5 cm (illustrated in FIG. 2) such that the scale between the sonographic image 90 and each reference circle remains 1:1. Thus, the various reference circles displayed in the third display area 50 may be used by a medical professional in determining a preferred catheter size for insertion within a patient, regardless of a chosen insertion depth.

Referring to FIG. 3, a user according to certain embodiments may select and position a reference circle 61 within the second display area 30. Overlaying the reference circle 61 on the sonographic image 90 allows the user to more accurately compare the size of the reference circle 61 with vascular structures, organs or other bodily parts represented by the sonographic image 90 in the second display area 30.

The selected reference circle size may correspond to one of the reference circles 51, 53, 55, 57, 59 displayed in the third display area 50. In addition, or in other embodiments, the user may select a reference circle size for display in the second display area 30 that is not displayed in the third display area 50. For example, as shown in FIG. 3, the reference circle 61 corresponding to the outer diameter of a 7 French catheter size has been positioned over the sonographic image 90 in the second display area 30.

In certain embodiments, the user may place the reference circle 61 within the second display area 30 by selecting it from the third display area 50 and dragging (or otherwise repositioning) it to a desired location within the second display area. The user may use, for example, a touch screen, a mouse, an action button 60, a keyboard, combinations of the foregoing, or other input devices to make the selection and position the reference circle 61 over the sonographic image 90 within the second display area 30. The user may also use such inputs to resize the reference circle 61 after positioning it within the second display area 30.

While FIGS. 1-3 illustrate the sonographic image 90 and the reference circles 51, 53, 55, 57, 59 displayed in different display areas (the second display area 30 and the third display area 50, respectively), the disclosure herein is not so limited. Indeed, an artisan will recognize from the disclosure herein that both the sonographic image 90 and the reference circles 51, 53, 55, 57, 59 may be displayed in the same display area of the user interface 10. For example, the sonographic image 90 and the reference circles 51, 53, 55, 57, 59 may each be displayed in the second display area 30.

In certain embodiments, the user interface 10 illustrated in FIGS. 1-3 may include various types of control objects to provide input and output functionality. Examples of suitable control objects include, without limitation, push buttons, by which a user may indicate acceptance of a particular action, radio buttons for selecting one of a number of available choices for a particular parameter, and check boxes for activating or deactivating various features. Additional examples of control objects include scroll bars for displaying different portions of a display area within a display window, sliders for adjusting variable values, and minimization buttons for displaying or hiding the contents of a folder or a pop-up menu.

In many embodiments, a user may activate one or more of these various control objects by touching the control object on a touch-sensitive display screen. In another embodiment, in a case where the display connected to the ultrasound device is a computer monitor, a user may activate one or more of these various control objects by positioning a cursor above the control object using a user input device (such as a mouse) connected to the ultrasound device and actuating the object by pushing a button or the like on the user input device.

In one embodiment, the user interface 10 illustrated in FIGS. 1-3 may include a plurality of action buttons 60. In at least one embodiment, the action buttons 60 may correspond to, and allow a user to select, various actions or functions that may be performed. Examples of actions that may be performed upon actuation of the action buttons 60 may include, without limitation: 1) a print operation for printing the area displayed within the second display area 30; 2) a save operation for saving an image of the picture displayed in the second display area 30; 3) a freeze operation for freezing a live picture displayed within the second display area 30; 4) a depth marker operation for allowing a user to select and position one or more depth markers within the second display area 30; 5) a grid operation for allowing a user to selectively display or hide reference lines 32, 34 and/or reference marks 36, 38; and 6) a reference circle operation for allowing a user to select and position a reference circle 51, 53, 55, 57, 59 within the second display area 30.

As seen in FIGS. 1-3, the user interface 10 may also include a display attribute interface 70. In at least one embodiment, a user may adjust various display attributes, such as the contrast, brightness, or hue of the display device by interacting with the display attribute interface 70. In addition, the user interface 10 may also include a power indicator 80. In certain embodiments, the power indicator 80 is configured to display the amount of charge remaining in a battery used to power the ultrasound device and the accompanying display device.

Figure 4:
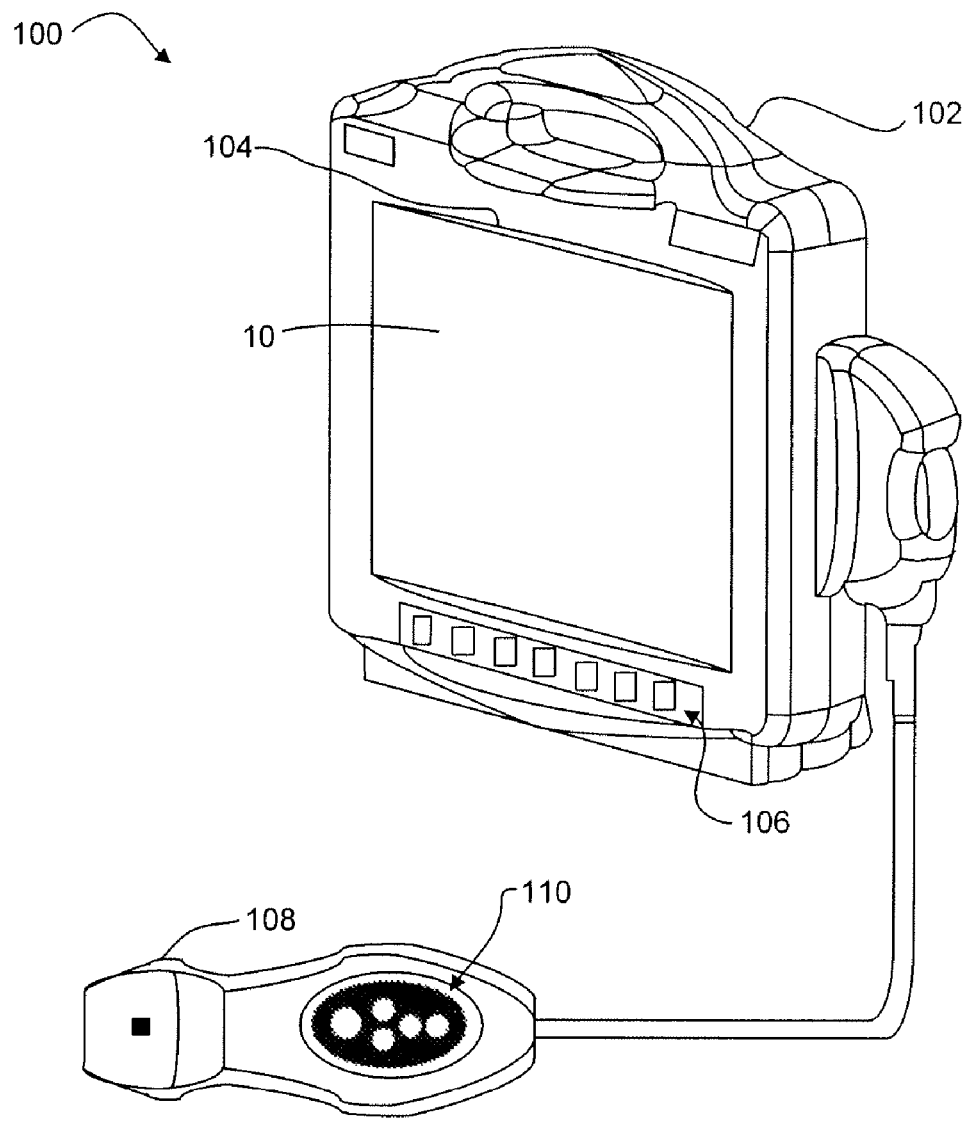
FIG. 4 is a semi-schematic perspective view of a sonographic system for providing a user interface of the type illustrated in FIGS. 1-3 according to one embodiment.

Referring to FIG. 4, there is shown a semi-schematic perspective view of a sonographic system 100 for providing a user interface 10 of the type illustrated in FIGS. 1-3. The sonographic system 100 may include, in one embodiment, a housing 102 including a display device 104 and one or more user controls 106. In one embodiment, the sonographic system 100 also includes a probe 108 including one or more user controls 110. The probe 108 is configured to transmit ultrasonic signals and to receive reflected ultrasonic signals. The sonographic system 100 processes the received ultrasonic signals for display on the display device 104 as discussed herein.

The user controls 106 may include, for example, image gain controls to adjust the amplification of a received ultrasonic signal, image depth controls to image structures at different depths and adjust the focus of a sonograph displayed on the display device 104, depth marker controls to selectively display depth markers and/or grid lines as discussed above, print and/or save controls to print/save an image currently displayed on the display device 10, image freeze controls to pause an image currently displayed on the display device 10, time/date set controls, and other controls for operating the sonographic system 100 as discussed herein. Such controls, or a subset thereof, may also be included in the user controls 110 on the probe 108 and/or on the display device (e.g., selectable using a touch screen). In addition, or in other embodiments, the functionality of the user controls 106, 110 may be provided by a keyboard, mouse, or other suitable input device.

Figure 5:
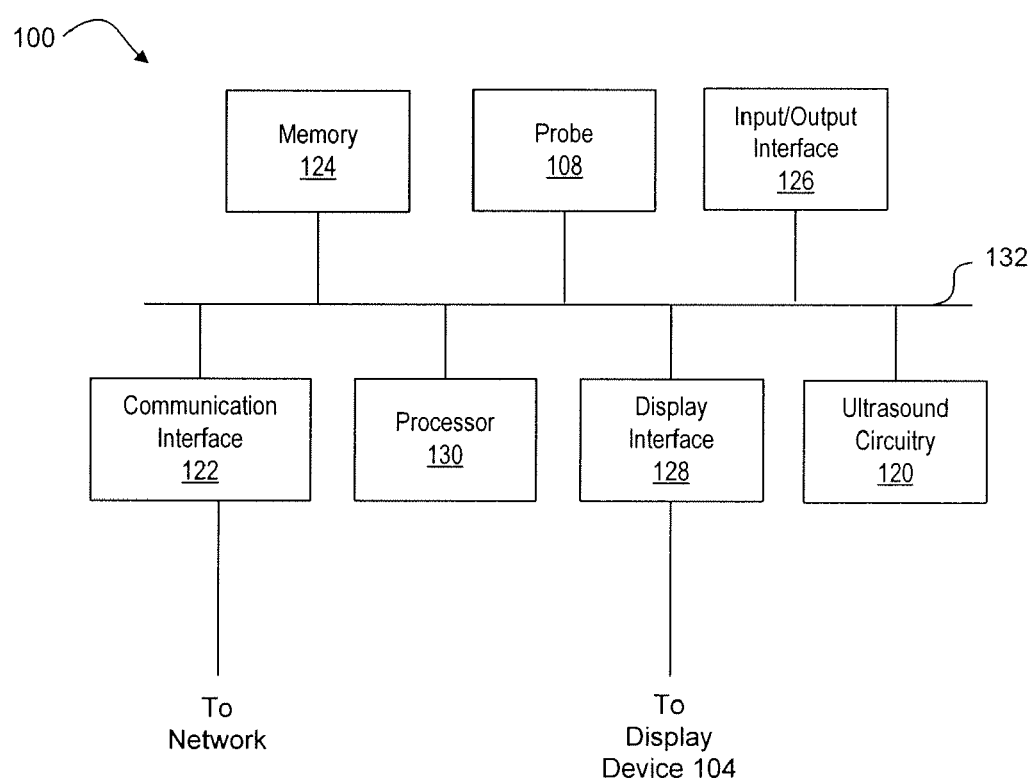
FIG. 5 is a schematic block diagram of a sonographic system according to one embodiment.

FIG. 5 is a schematic block diagram of the sonographic system 100 according to one embodiment. The illustrated components may be implemented using any suitable combination of hardware, software, and/or firmware. In one configuration, the sonographic system 100 includes ultrasound circuitry 120 for generating, transmitting, and processing ultrasound signals, as is known to one skilled in the art. All or a portion of the ultrasound circuitry 120 may be included within the probe 108. One skilled in the art will recognize that at least a portion of the ultrasound circuitry 120 may also be included within the housing 102.

The sonographic system 100 may also include, according to one embodiment, a communication interface 122 for communicating with a network such as the Internet or World Wide Web, an intranet such as a local area network (LAN) or a wide area network (WAN), a public switched telephone network (PSTN), a cable television network (CATV), or any other network of communicating computerized devices.

The sonographic system 100 may further include a memory 124, such as a random access memory (RAM), hard drives, floppy diskettes, optical disks, CD-ROMs, DVD-ROMs, ROMs, RAMs, EPROMs, EEPROMs, magnetic or optical cards, and/or solid-state memory devices. The memory 124 may store an operating system (OS) for the sonographic system 100 (e.g., a Windows CE® OS or a Linux® OS), application program code, and various types of data. In one embodiment, the memory 124 stores sonographic images 90 and/or images of reference circles 51, 53, 55, 57, 59, as illustrated in FIGS. 1-3.

An input/output interface 126 may be provided for receiving commands from an input device, such as a mouse, keyboard, or remote control. The input/output interface 126 may detect, for example, a user pressing the user controls 106, 110. The input/output interface 126 may also send data to an output device, such as a printer or external storage device.

The sonographic system 100 may further include a display interface 128 for rendering graphical data, including the user interface 10, on the display device 104 and/or an external display device.

A processor 130 controls the operation of the sonographic system 100, including the other components described above, which may be in electrical communication with the processor 130 via a bus 132. The processor 130 may be embodied as a microprocessor, a microcontroller, a digital signal processor (DSP), or other device known in the art. The processor 130 may perform logical and arithmetic operations based on program code and data stored within the memory 124 or an external storage device.

Of course, FIG. 5 illustrates only one possible configuration of a sonographic system 100. An artisan will recognize that various other architectures and components may be provided.

Figure 6:
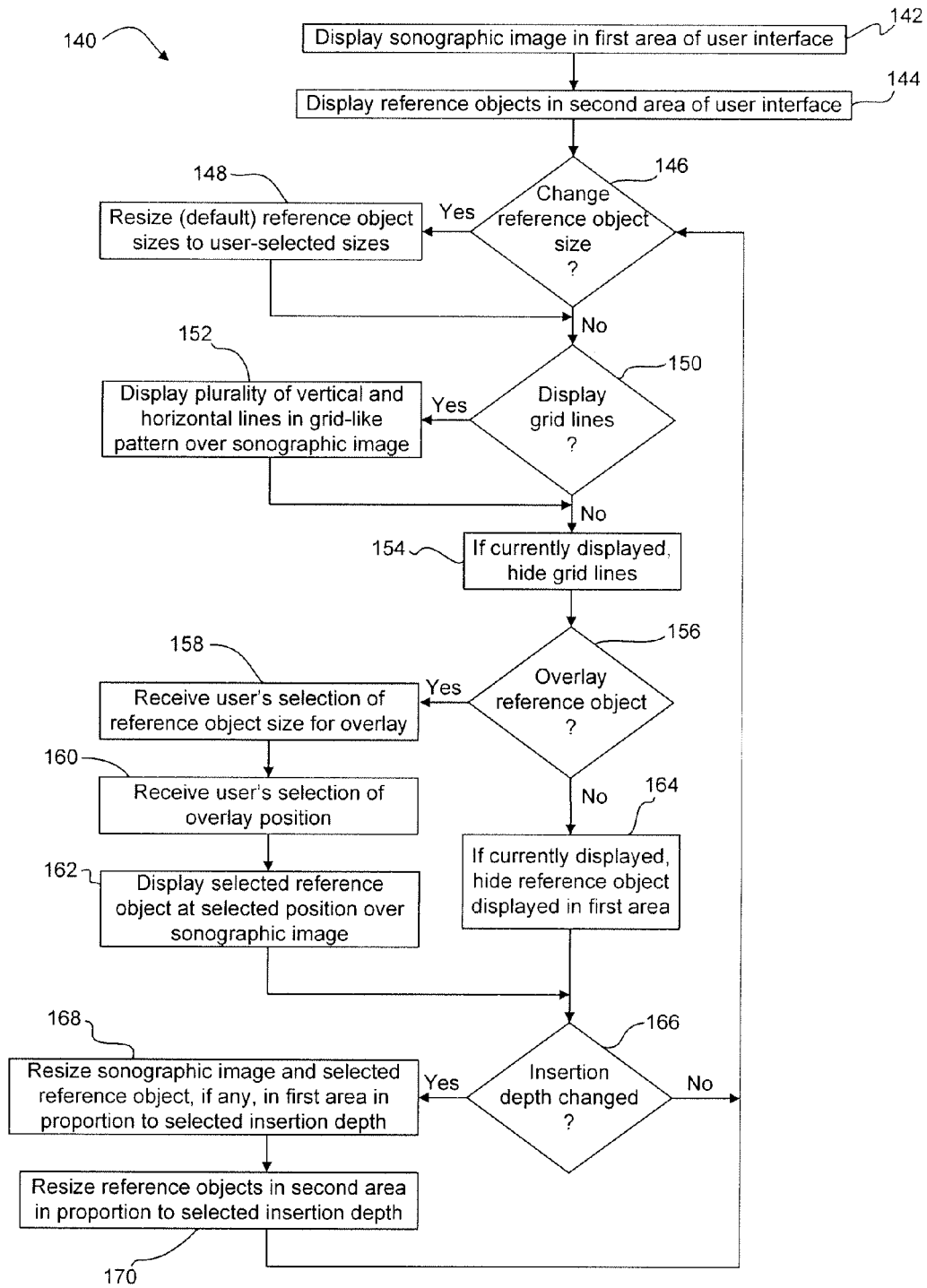
FIG. 6 is a flowchart of a method for displaying a sonographic image according to certain embodiments.

FIG. 6 is a flowchart of a method 140 for displaying a sonographic image according to certain embodiments. The method 140 includes displaying 142 a sonographic image in a first area of a user interface and displaying 144 reference objects in a second area of a user interface. The reference objects may include, for example, the reference circles 51, 53, 55, 57, 59 shown in FIGS. 1-3. Of course, however, the reference objects are not so limited and may be of any shape. As discussed herein, a dimension of the reference objects correspond to a dimension of a device configured to be inserted or implanted within a patient's body.

In one embodiment, the method 140 also includes determining 146 whether a user has requested a change in the size of one or more of the reference objects displayed in the second area of the user interface. If a change has been requested, the method 140 includes resizing 148 the default sizes of the reference objects based on the user's request. For example, the user may request that the size of a particular reference object corresponding to a 6 French catheter size be changed so as to correspond to a 7 French catheter size.

In one embodiment, the method 140 also includes determining 150 whether a user has requested that grid lines be displayed over the sonographic image in the first area of the user interface. If the user has turned on the grid lines, the method 140 displays 152 a plurality of vertical and horizontal lines in a grid-like pattern over the sonographic image. As discussed above, an area defined by a first vertical line and a second vertical line adjacent to the first vertical line corresponds to a dimensional measurement unit. Similarly, an area defined by a first horizontal line and a second horizontal line adjacent to the first horizontal line corresponds to a dimensional measurement unit. If the user has turned off the grid lines, the method 140 hides 154 any grid lines displayed in the first area of the user interface.

In one embodiment, the method 140 also includes determining 156 whether a user has requested that a selected reference object be overlaid on the sonographic image in the first area of the user interface. If yes, the method 140 includes receiving 158 the user's selection of a reference object size for the overlay. As discussed above, the user may select the size by selecting one of the reference objects displayed in the second area of the user interface. In addition, or in another embodiment, the user may define a size that does not correspond to any reference objects displayed in the second area of the user interface.

The method 140 also receives 160 the user's selection of an overlay position within the first area of the user interface. As discussed above, the user may position the selected reference object by dragging it (e.g., using a touch sensitive screen or mouse), using arrows (e.g., on a touch sensitive screen, display device, or keyboard), or otherwise defining the coordinates (e.g., using a keyboard) where the reference object is moved or placed. The method 140 then displays 162 the selected reference object at the selected position over the sonographic image in the first area of the user interface. If the user turns off the overlay, the method 140 hides 164 the selected reference object displayed in the first area of the user interface.

In one embodiment, the method 140 determines 166 whether a user has changed an insertion depth (imaging depth). If the insertion depth has been changed, the method 140 resizes 168 the sonographic image and the selected reference object, if any, displayed in the first area of the user interface in proportion to the selected insertion depth. Although not shown in FIG. 6, in one embodiment, the method 140 also adjusts the distance between lines in the grid, if displayed, in proportion to the selected insertion depth. In another embodiment, the method may change the dimensional measurement unit corresponding to the area defined by successive vertical and/or horizontal lines in the grid, if displayed, in proportion to the selected insertion depth.

The method 140 also resizes 170 the reference objects displayed in the second area of the user interface in proportion to the selected insertion depth. Thus, as the insertion depth changes such that the sonographic image displayed in the first area of the user interface is enlarged (zoom in) or reduced (zoom out), the respective sizes of the reference objects (whether displayed in the first or second area of the user interface) are maintained relative to the size of a vascular structure, organ, or other bodily structure represented in the sonographic image. Accordingly, a user may determine the reference object size most suitable or desired for the particular vascular structure, organ, or other bodily structure.

Various modifications, changes, and variations apparent to those of skill in the art may be made in the arrangement, operation, and details of the methods and systems of the disclosure without departing from the spirit and scope of the disclosure. Thus, it is to be understood that the embodiments described above have been presented by way of example, and not limitation, and that the invention is defined by the appended claims.

What is claimed is:

1. A display device for a sonographic device, the display device comprising:
    a user interface that displays a live sonographic image and at least a first virtual reference object;
    wherein the first virtual reference object represents a medical instrument and is movable independent from the medical instrument; and
    wherein the user interface automatically scales the first virtual reference object in proportion to the live sonographic image such that the scale between the live sonographic image and the virtual reference object remains 1:1.

2. The display device of claim 1, wherein the user interface displays a plurality of vertical lines and a plurality of horizontal lines arranged in a grid-like pattern and placed over the live sonographic image.

3. The display device of claim 2, wherein an area defined by a first vertical line and a second vertical line adjacent to the first vertical line corresponds to a dimensional measurement unit.

4. The display device of claim 2, wherein an area defined by a first horizontal line and a second horizontal line adjacent to the first horizontal line corresponds to a dimensional measurement unit.

5. The display device of claim 1, wherein the displayed size of both the live sonographic image and the first virtual reference object changes in proportion to a chosen insertion depth.

6. The display device of claim 1, wherein the first virtual reference object comprises a circle including a diameter corresponding to an outer diameter of the medical instrument, and wherein the user interface allows a user to select the first virtual reference object based on the outer diameter of the medical instrument desired.

7. The display device of claim 1, wherein the user interface displays the live sonographic image in a first display area and the first virtual reference object in a second display area, and wherein the user interface selectively displays a second virtual reference object over the live sonographic image in the first display area.

8. The display device of claim 7, wherein the user interface allows a user to select and position one or more depth markers within the second display area.

9. The display device of claim 1, wherein the first virtual reference object is a predefined template representing the medical instrument.

10. The display device of claim 1, wherein the first virtual reference object represents a catheter.

11. The display device of claim 1, wherein the user interface includes an insertion depth indicator that displays an insertion depth of the live sonographic image.

12. The display device of claim 1, wherein the user interface includes a plurality of action buttons allowing a user to select various actions or functions to be performed.

13. The display device of claim 12, wherein at least one of the plurality of action buttons allows a user to perform a freeze operation for freezing the live sonographic image.

14. A method for selecting a size of a medical instrument, the method comprising:
    displaying a live sonographic image of an internal structure of a body in a user interface;
    displaying a virtual reference object in the user interface, the virtual reference object representing a selected size of a medical instrument and being movable independent from the medical instrument; and
    automatically scaling the virtual reference object in proportion to the live sonographic image such that the scale between the live sonographic image and the virtual reference object remains 1:1 to allow comparison of the virtual reference object to the internal structure of the body.

15. The method of claim 14, further comprising displaying a plurality of vertical and horizontal lines arranged in a grid-like pattern over the live sonographic image.

16. The method of claim 15, further comprising scaling the distance between successive vertical lines and successive horizontal lines to correspond to a dimensional measurement unit.

17. The method of claim 15, wherein displaying the plurality of vertical and horizontal lines comprises allowing a user to selectively display and hide the plurality of vertical and horizontal lines.

18. The method of claim 14, further comprising scaling the displayed size of both the live sonographic image and the virtual reference object in proportion to a user selected insertion depth.

19. The method of claim 14, further comprising allowing a user to select the size of the medical instrument corresponding to the virtual reference object.

20. The method of claim 14, further comprising selectively displaying the virtual reference object over the live sonographic image.

21. The method of claim 20, wherein selectively displaying comprises:
    displaying the live sonographic image in a first area of the user interface;
    displaying the virtual reference object in a second area of the user interface; and
    allowing the user to drag the virtual reference object from the second area to a desired location in the first area of the user interface.

22. The method of claim 14, further comprising selecting a size of a catheter for use in a vascular structure.

23. The method of claim 14, further comprising comparing the virtual reference object to the live sonographic image of the internal structure of the body at multiple insertion depths.

24. A computer accessible medium comprising program instructions for causing a computer to perform a method for facilitating selection of a size of a medical instrument, the method comprising:
    displaying a live sonographic image of a vascular structure in a user interface;

displaying a virtual reference object in the user interface, the virtual reference object is a predefined template representing a medical instrument of a selected size and is movable independent from the medical instrument; and automatically scaling the virtual reference object in proportion to the live sonographic image such that the scale between the live sonographic image and the virtual reference object remains 1:1 to allow comparison of the virtual reference object to the vascular structure.

25. A sonographic system, comprising:

a probe that transmits ultrasonic signals and receives reflected ultrasonic signals, the probe including one or more user controls;

a housing including a display device, the display device comprising a user interface that displays a sonographic image based on reflected ultrasonic signals received by the probe and at least a first virtual reference object, the first virtual reference object representing a medical instrument, the first virtual reference object movable independent from the represented medical instrument, the user interface scaling the first virtual reference object in proportion to the sonographic image.

26. The sonographic system of claim 25, wherein the sonographic image is a live sonographic image.

27. The sonographic system of claim 26, wherein the user interface automatically scales the first virtual reference object in proportion to the live sonographic image such that the scale between the live sonographic image and the first virtual reference object remains 1:1.

28. The sonographic system of claim 25, wherein the probe and housing are connected by a cable.

29. The sonographic system of claim 25, further comprising ultrasound circuitry for generating, transmitting, and processing ultrasound signals, a portion of the ultrasound circuitry included within the housing.

* * * * *